United States Patent [19]
Wakabayashi et al.

[11] 4,292,070
[45] Sep. 29, 1981

[54] N-SUBSTITUTED TETRAHYDROPHTHALIMIDE AND HERBICIDAL COMPOSITION

[75] Inventors: Osamu Wakabayashi, Kawasaki; Kuni Matsuya, Zama; Hiroki Ohta, Machida; Tetsuo Jikihara, Kawasaki; Seiichi Suzuki, Yokohama, all of Japan

[73] Assignee: Mitsubishi Chemical Industries, Ltd., Tokyo, Japan

[21] Appl. No.: 133,270

[22] Filed: Mar. 24, 1980

[30] Foreign Application Priority Data

Apr. 13, 1979 [JP] Japan .................. 54-44948
Apr. 13, 1979 [JP] Japan .................. 54-44951

[51] Int. Cl.³ .................. A01N 43/38; C07D 209/48
[52] U.S. Cl. .................. 71/96; 260/326 A
[58] Field of Search .................. 260/326 A; 71/96

[56] References Cited

U.S. PATENT DOCUMENTS

| 3,654,302 | 4/1972 | Schwartz et al. | 260/326 A |
| 3,745,170 | 7/1973 | Fujinami et al. | 260/326.5 |
| 3,878,224 | 4/1975 | Matsui et al. | 260/326 A |
| 3,984,435 | 10/1976 | Matsui et al. | 260/326 A |
| 4,001,272 | 1/1977 | Goddard | 71/96 |
| 4,032,326 | 6/1977 | Goddard | 71/96 |

FOREIGN PATENT DOCUMENTS 2165651  4/1973  Fed. Rep. of Germany.
50-88225  7/1975  Japan ..................... 71/96

Primary Examiner—Donald G. Daus
Assistant Examiner—M. C. Eakin
Attorney, Agent, or Firm—Oblon, Fisher, Spivak, McClelland & Maier

[57] ABSTRACT

N-substituted-3,4,5,6-tetrahydrophthalimides in which the N-substituted group is a phenyl group having a substituted-oxy group at 3-position and a chlorine or bromine atom at 4-position and chlorine or hydrogen atom at 2-position have excellent herbicidal effect and are used as selective herbicides in a plant culturing.

14 Claims, No Drawings

N-SUBSTITUTED TETRAHYDROPHTHALIMIDE AND HERBICIDAL COMPOSITION

BACKGROUND OF THE INVENTION

The present invention relates to novel N-substituted tetrahydrophthalimides and herbicidal compositions thereof.

N-substituted aryl-$\Delta'$-tetrahydrophthalimide derivatives having herbicidal activity have been reported.

For example, Japanese Examined Patent Publication No. 11940/1973 (U.S. Pat. No. 3,878,224 and U.S. Pat. No. 3,984,435 and West German Unexamined Patent Publication No. 2,165,651) discloses N-substituted-$\Delta'$-tetrahydrophthalimide which is represented by the general formula

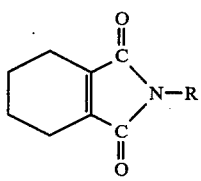

wherein R may be an aryl, aralkyl or benzyl optionally substituted with 1 to 5 halogen atoms; hydroxy, alkoxy, nitro, cyano, thiocyano, carboxy, halogenated alkyl, alkyl, phenyl and OCH$_2$A (where A is phenyl or naphthyl) group and the like may also be substituted therein. N-(4-chloro-3-methoxyphenyl)-$\Delta'$-tetrahydrophthalimide and N-(4-bromo-3-methoxyphenyl)-$\Delta'$-tetrahydrophthalimide are described as the exemplified compounds having the formula wherein R is a halogen- and alkoxy-substituted phenyl group.

U.S. Pat. No. 4,001,272 and U.S. Pat. No. 4,032,326 disclose herbicidal 2-substituted aryl-4,5,6,7-tetrahydro-2H-isoindole-1,3-diones of the following formula

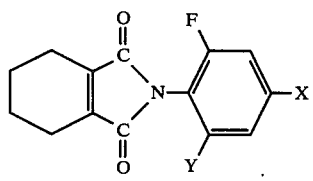

wherein X is Cl, Br or F and Y is H or F.

The inventors have studied novel tetrahydrophthalimides as an active ingredient of a herbicidal composition and have found that the specific novel N-aryl-3,4,5,6-tetrahydrophthalimides have excellent herbicidal effect.

SUMMARY OF THE INVENTION

The present invention is to provide novel N-substituted 3,4,5,6-tetrahydrophthalimides which are represented by the general formula

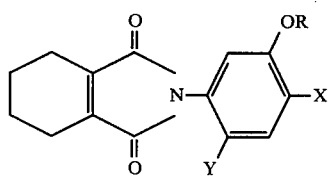

wherein X represents chlorine or bromine atom; Y represents chlorine or hydrogen atom; R represents an alkenyl, alkynyl aralkyl, aryloxy-alkyl, alkyl which has two or more carbon atoms or cycloalkyl group; a process for producing the same; and herbicidal compositions containing the same as an active ingredient.

DETAILED DESCRIPTION OF THE PREFERRED EMBODIMENTS

The N-substituted-3,4,5,6-tetrahydrophthalimides represented by the general formula (I) of the present invention can be produced by the following processes.

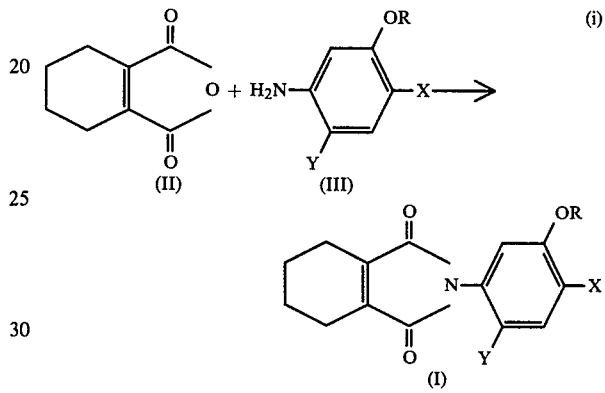

wherein X, Y and R are defined above.

The object compound (I) is obtained by reacting tetrahydrophthalic anhydride with the corresponding aniline at 70° to 200° C. in the absence of a solvent or in the presence of a solvent such as acetic acid, toluene and water.

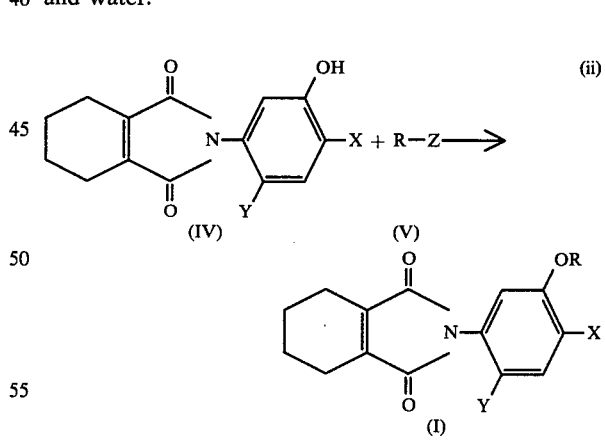

wherein X, Y and R are defined above and Z represents a halogen atom such as chlorine atom.

The object compound (I) is obtained by reacting N-(3-hydroxyphenyl)-3,4,5,6-tetrahydrophthalimide or it's halogen derivative with the corresponding halide at 0° to 150° C. in a solvent such as acetone, benzene, N,N-dimethylformamide in the presence of a base such as sodium carbonate, potassium carbonate, sodium hydroxide and potassium hydroxide.

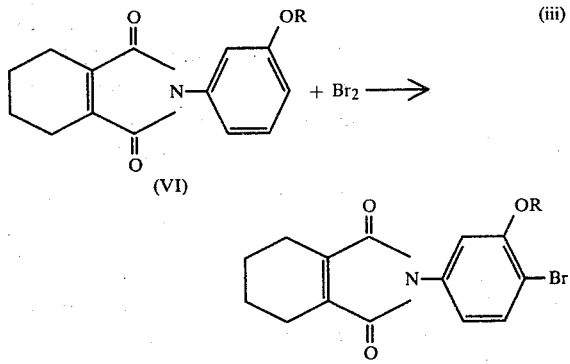

The object compound (I) wherein X is bromine atom and Y is hydrogen atom can be obtained by the reaction (iii) in a solvent such as acetic acid, benzene and chloroform.

The object compound (I) can be obtained by brominating the compound having the formula

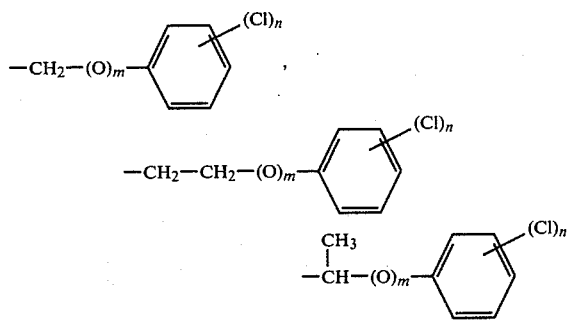

by the reaction (iii) and then, reacting the resulting product with the compound R-Z by the reaction (ii).

Suitable anilines (II) and halides (V) used as the reagents include the compounds (II) or (V) wherein R is a $C_3$-$C_4$ alkenyl group such as allyl or methallyl group; a $C_3$-$C_4$ alkynyl group such as propargyl group; a cycloalkyl group such as cyclopentyl, cyclohexyl and cycloheptyl group; a $C_2$-$C_{12}$ straight or branched alkyl group; 4-chlorobenzyl, α-methylbenzyl, phenethyl and 2,4-dichlorophenoxyethyl group which are represented by the formula

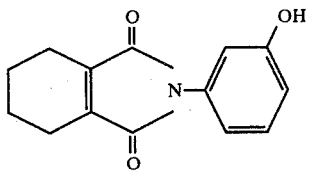

wherein m is 0 or 1; n is 0, 1 or 2; and chlorine atom is in 2-position and/or 4-position.

The processes for producing the compounds (I) of the present invention will be illustrated by certain examples which are provided for purposes of illustration only and are not intended to be limiting the present invention.

EXAMPLE 1

A mixture of 3.47 g. of 2-chloro-5-nitrophenol, 3.74 g. of propyl iodide, 3.04 g. of anhydrous potassium carbonate and 20 ml. of acetone was refluxed with stirring for 6 hours to obtain 3.80 g of 4-chloro-3-propoxynitrobenzene having a melting point of 52° to 53° C.

The nitrobenzene derivatives shown in the following table were also produced by the similar reaction using the corresponding reagents.

TABLE 1

| R | Physical property | R | Physical property |
|---|---|---|---|
| iso-$C_3H_7$ | m.p. 57.5–59° C. | —$(CH_2)_6CH_3$ | $n_D^{26}$ 1.5287 |
| n-$C_4H_9$ | m.p. 47–48° C. | —$CH_2$—Ph | m.p. 109–110° C. |
| n-$C_5H_{11}$ | $n_D^{24.5}$ 1.5410 | —$CH_2$—Ph—Cl | m.p. 150–151° C. |

The product was reduced by mixing, 3.02 g. of 4-chloro-3-propoxynitrobenzene, 11.0 g. of iron powder and 1 ml. of acetic acid in 90 ml. of water and heating the mixture at 90° C. with stirring for 10 hours to obtain 2.25 g. of oily 4-chloro-3-propoxyaniline having a refractive index of 1.5658 (17° C.).

The 4-chloro-3-alkoxyanilines shown in Table 2 were also produced by the similar reaction.

TABLE 2

| R | Physical property | R | Physical property |
|---|---|---|---|
| iso-$C_3H_7$ | $n_D^{27}$ 1.5592 | —$(CH_2)_6CH_3$ | $n_D^{25.5}$ 1.5340 |
| n-$C_4H_9$ | $n_D^{17}$ 1.5566 | —$CH_2$—Ph | m.p. 63–65° C. |
| n-$C_5H_{11}$ | $n_D^{24.5}$ 1.5470 | —$CH_2$—Ph—Cl | m.p. 103–104° C. |

EXAMPLE 2

A mixture of 15.2 g. of 3,4,5,6-tetrahydrophthalic anhydride, 14.4 g. of 3-hydroxy-4-chloroaniline and 50 ml. of glacial acetic acid was refluxed with stirring for 2 hours and then, the reaction mixture was cooled to a room temperature and water was added to precipitate a crystal and the crystal was separated by a filtration and recrystallized from isopropanol to obtain N-(4-chloro-3-hydroxyphenyl)-3,4,5,6-tetrahydrophthalimide (m.p.: 236.5°–238° C.; yellow crystal) (yield: 87.5%).

EXAMPLE 3

A mixture of 3,4,5,6-tetrahydrophthalic anhydride, 3-hydroxyaniline and a glacial acetic acid was heated to obtain N-(3-hydroxyphenyl)-3,4,5,6-tetrahydrophthalimide (m.p.: 199° to 201° C.) and 40.6 g. of the product was dissolved into 600 ml. of glacial acetic acid and 27.2 g. of bromine was added dropwise at 30° to 40° C. and the mixture was stirred at a room temperature for 5 hours to precipitate a crystal. The crystal was separated by a filtration and washed with methanol and recrystallized from benzene-tetrahydrofuran to obtain N-(4- bromo-3-hydroxyphenyl)-3,4,5,6-tetrahydrophthalimide (m.p.: 247°–248° C.; yellow crystal) (yield: 88%).

EXAMPLE 4

A mixture of 33.4 g. of 3,4,5,6-tetrahydrophthalic anhydride, 35.6 g. of 3-hydroxy-2,4-dichloroaniline and 130 ml. of glacial acetic acid was refluxed with stirring for 2 hours and the mixture was cooled to a room temperature and water was added to the mixture to precipitate a crystal. The crystal was separated by a filtration and recrystallized from benzene-n-hexane to obtain N-(2,4-dichloro-5-hydroxyphenyl)-3,4,5,6-tetrahydrophthalimide (m.p.: 155°–157° C.: white crystal) (yield: 75%).

EXAMPLE 5

A mixture of 0.5 g. of 3,4,5,6-tetrahydrophthalic anhydride, 0.7 g. of 4-chloro-3-benzyloxyaniline and 2 ml. of glacial acetic acid was refluxed with stirring for 1.5 hours and the reaction mixture was cooled to a room temperature and water was added to precipitate a crystal. The crystal was separated by a filtration and washed with water and recrystallized from ethyl acetate-methanol to obtain 0.95 g. of N-(4-chloro-3-benzyloxyphenyl)-3,4,5,6-tetrahydrophthalimide which is shown in Table 3 as Compound No. 10.

Compounds No. 13 and No. 22 shown in Table 3 were produced by the similar process.

EXAMPLE 6

A mixture of 1.67 g. of N-(4-chloro-3-hydroxyphenyl)-3,4,5,6-tetrahydrophthalimide, 0.87 g. of allyl bromide, 0.91 g. of anhydrous potassium carbonate and 20 ml. of acetone was refluxed with stirring for 3 hours and the reaction mixture was cooled to a room temperature and 2 N—HCl was added to precipitate a crystal. The crystal was separated by a filtration and washed with water and purified by a chromatography on a column of silica gel with benzene to obtain 1.63 g. of N-(4-chloro-3-allyloxyphenyl)-3,4,5,6-tetrahydrophthalimide (Compound No. 1 shown in Table 3).

Compounds No. 2, 3, 4, 5 and 6 shown in Table 3 were also produced by the similar process.

EXAMPLE 7

A mixture of 1.56 g. of N-(2,4-dichloro-5-hydroxyphenyl)-3,4,5,6-tetrahydrophthalimide, 0.54 g. of methallyl chloride, 0.76 g. of anhydrous potassium carbonate, 0.17 g. of potassium iodide and 20 ml. of acetone was refluxed with stirring for 6.5 hours and the mixture was cooled to a room temperature and 2 N—HCl was added to precipitate a crystal. The crystal was separated by a filtration and washed with water and purified by a chromatography on a column of silica gel with benzene to obtain 1.53 g. of N-(2,4-dichloro-5-methallyloxyphenyl)-3,4,5,6-tetrahydrophthalimide (Compound No. 9 shown in Table 3).

Compounds No. 7, 8, 11, 12, 14, 15 and 16 shown in Table 3 were also produced by the similar process.

EXAMPLE 8

A mixture of 1.07 g. of heptyl bromide, 1.0 g. of potassium iodide and 20 ml. of acetone was refluxed with stirring for 1 hour and the reaction mixture was cooled to a room temperature, and 1.61 g. of N-(4-bromo-3-hydroxyphenyl)-3,4,5,6-tetrahydrophthalimide and 0.83 g. of anhydrous potassium carbonate were added and the mixture was refluxed with stirring for 11 hours. Acetone was distilled off from the reaction mixture under a reduced pressure, then 2 N—HCl was added and extracted with ethyl acetate. The organic phase was washed with water and dehydrated over anhydrous sodium sulfate. The solvent was distilled off and the residue was purified by chromatography on a column of silica gel with benzene to obtain 1.37 g. of N-(4-bromo-3-heptyloxyphenyl)-3,4,5,6-tetrahydrophthalimide (Compound No. 23 shown in Table 3).

Compounds No. 17, 18, 19, 20, 21, 22, 24, 25, 26, 27, 28, 29 and 30 were also produced by the similar process.

EXAMPLE 9

A mixture of 1.10 g. of isopropyl bromide, 0.83 g. of potassium iodide and 20 ml. of acetone was refluxed with stirring to obtain a reaction mixture containing isopropyl iodide and 1.25 g. of 4-(2,4-dichloro-3-hydroxyphenyl)-3,4,5,6-tetrahydrophthalimide and 0.81 g. of anhydrous potassium carbonate were added and the mixture was refluxed with stirring for 8 hours to obtain 1.28 g. of N-(2,4-dichloro-3-isopropoxyphenyl)-3,4,5,6-tetrahydrophthalimide.

Various tetrahydrophthalimides were produced by the similar process. The resulting compounds and the physical properties thereof are shown in Table 3 as Compounds No. 33, 36, 39, 42, 44, 46, 48, 50, 52 and 53.

EXAMPLE 10

A mixture of 0.82 g. of butyl bromide, 1.00 g. of potassium iodide and 20 ml. of acetone was refluxed with stirring to obtain a reaction mixture containing butyl iodide and 1.61 g. of N-(4-bromo-3-hydroxylphenyl)-3,4,5,6-tetrahydrophthalimide and 0.83 g. of anhydrous potassium carbonate were added and the mixture was refluxed with stirring for 10 hours to obtain 1.58 g. of N-(4-bromo-3-butoxyphenyl)-3,4,5,6-tetrahydrophthalimide.

Various tetrahydrophthalimides were produced by the similar process. The resulting compounds and physical properties thereof are shown in Table 3 as Compounds No. 32, 35, 38, 41, 43, 45, 47 and 49.

EXAMPLE 11

A mixture of 0.92 g. of 4-chloro-3-propoxyaniline, 0.84 g. of 3,4,5,6-tetrahydrophthalic acid anhydride and 8 ml. of acetic acid was refluxed with stirring to obtain 1.34 g. of N-(4-chloro-3-propoxyphenyl)-3,4,5,6-tetrahydrophthalimide.

Compounds No. 31, 34, 37, 40 and 51 shown in Table 3 were also produced by the similar process.

Typical compounds (I) of the present invention produced by these processes are shown in Table 3. The structures of the compounds shown in Table 3 were confirmed by IR spectrum and NMR spectrum.

TABLE 3

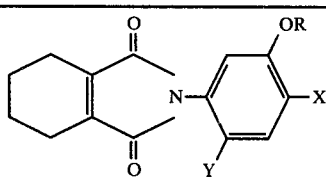

| No. | X | Y | R | mp (°C.) |
|---|---|---|---|---|
| 1 | Cl | H | —CH$_2$CH=CH$_2$ | 124~125 |
| 2 | Br | H | —CH$_2$CH=CH$_2$ | 115~116 |
| 3 | Cl | Cl | —CH$_2$CH=CH$_2$ | 73.5~74.5 |
| 4 | Cl | H | —CH$_2$C≡CH | 145.5 |
| 5 | Br | H | —CH$_2$C≡CH | 154~155 |

TABLE 3-continued

[Structure: tetrahydrophthalimide with N-phenyl bearing OR, X, Y substituents]

| No. | X | Y | R | Physical property |
|---|---|---|---|---|
| 6 | Cl | Cl | —CH₂C≡CH | 147.5~149 |
| 7 | Cl | H | —CH₂C=CH₂ \| CH₃ | 112.5~113 |
| 8 | Br | H | —CH₂C=CH₂ \| CH₃ | 113~114 |
| 9 | Cl | Cl | —CH₂C=CH₂ \| CH₃ | 84.5~85 |
| 10 | Cl | H | —CH₂—(phenyl) | 117~118 |
| 11 | Br | H | —CH₂—(phenyl) | 113 |
| 12 | Cl | Cl | —CH₂—(phenyl) | 148~150 |
| 13 | Cl | H | —CH₂—(phenyl)—Cl | 105~106 |
| 14 | Cl | Cl | —CH₂—(phenyl)—Cl | 175.5~176.5 |
| 15 | Br | H | —CH(CH₃)—(phenyl) | 98~99 |
| 16 | Cl | Cl | —CH(CH₃)—(phenyl) | 109~110 |
| 17 | Br | H | —CH₂CH₂—(phenyl) | 100~101 |
| 18 | Cl | Cl | —CH₂CH₂—(phenyl) | 113~115.5 |
| 19 | Cl | Cl | —CH₂CH₂O—(phenyl)(Cl)(Cl) | 162~165 |
| 20 | Br | H | —(CH₂)₅CH₃ | 55~55.5 |
| 21 | Cl | Cl | —(CH₂)₅CH₃ | 88~89.5 |
| 22 | Cl | H | —(CH₂)₆CH₃ | 69~70 |
| 23 | Br | H | —(CH₂)₆CH₃ | 62.5~63.5 |
| 24 | Cl | Cl | —(CH₂)₆CH₃ | 68~68.5 |
| 25 | Br | H | —(CH₂)₉CH₃ | 50~51 |
| 26 | Cl | Cl | —(CH₂)₉CH₃ | 50~53 |
| 27 | Br | H | cyclopentyl | 118~118.5 |
| 28 | Cl | Cl | cyclopentyl | 93~94 |
| 29 | Cl | H | cyclohexyl | 110~111 |
| 30 | Br | H | cyclohexyl | 111~115 |
| 31 | Cl | H | $C_2H_5$ | mp 130~131° C. |
| 32 | Br | H | $C_2H_5$ | mp 134~135° C. |
| 33 | Cl | Cl | $C_2H_5$ | mp 145~146° C. |
| 34 | Cl | H | n-$C_3H_7$ | mp 101~102° C. |
| 35 | Br | H | n-$C_3H_7$ | mp 100~101° C. |
| 36 | Cl | Cl | n-$C_3H_7$ | mp 80~80.5° C. |
| 37 | Cl | H | iso-$C_3H_7$ | mp 120.5~122° C. |
| 38 | Br | H | iso-$C_3H_7$ | mp 131~132° C. |
| 39 | Cl | Cl | iso-$C_3H_7$ | mp 140~141° C. |
| 40 | Cl | H | n-$C_4H_9$ | mp 63~64° C. |
| 41 | Br | H | n-$C_4H_9$ | mp 70~70.5° C. |
| 42 | Cl | Cl | n-$C_4H_9$ | mp 118~119° C. |
| 43 | Br | H | iso-$C_4H_9$ | mp 94~96° C. |
| 44 | Cl | Cl | iso-$C_4H_9$ | mp 140~141° C. |
| 45 | Br | H | sec-$C_4H_9$ | mp 113~114° C. |
| 46 | Cl | Cl | sec-$C_4H_9$ | $n_D^{20}$ 1.5629 |
| 47 | Br | H | iso-$C_5H_{11}$ | mp 84~84.5° C. |
| 48 | Cl | Cl | iso-$C_5H_{11}$ | mp 140~141° C. |
| 49 | Br | H | sec-$C_5H_{11}$ | mp 103~105° C. |
| 50 | Cl | Cl | sec-$C_5H_{11}$ | mp 53~55° C. |
| 51 | Cl | H | n-$C_5H_{11}$ | mp 71~72° C. |
| 52 | Br | H | n-$C_5H_{11}$ | mp 61° C. |
| 53 | Cl | Cl | n-$C_5H_{11}$ | mp 115~117° C. |

Among these compounds (I) of the present invention, the compounds having superior herbicidal activity include the compounds represented by the formula (I) wherein R is propargyl, allyl, methallyl, cyclopentyl, cyclohexyl group or a $C_2$–$C_4$ straight or branched alkyl group.

It is especially suitable to apply the compounds represented by the formula (I) wherein R is allyl, propargyl or cyclopentyl group or wherein R is ethyl, propyl or isopropyl group and Y is hydrogen atom and X is chlorine or bromine atom in a soil treatment.

It is especially suitable to apply the compounds represented by the formula (I) wherein R is methallyl or cyclohexyl group or wherein Y is hydrogen atom, X is chlorine atom; and R is sec-butyl group in a flooded paddy field.

The compounds having remarkably superior herbicidal activity among the compounds (I) include N-(3-propargyloxy-4-bromophenyl)-3,4,5,6-tetrahydrophthalimide, N-(3-propargyloxy-4-chlorophenyl)-3,4,5,6-tetrahydrophthalimide, N-(3-isopropoxy-4-chlorophenyl)-3,4,5,6-tetrahydrophthalimide, N-(3-n-propoxy-4-chlorophenyl)-3,4,5,6-tetrahydrophthalimide, and N-(3-isopropoxy-4-bromophenyl)-3,4,5,6-tetrahydrophthalimide. Compounds No. 1, 2, 6, 7, 3, 27, 29, 31, 32, 35, 39, 40, 41 and 43 have also superior herbicidal activity.

The compounds (I) can be used as herbicides without an adjuvant. Thus, the compounds (I) are usually used in a form of herbicidal compositions such as an emulsifiable concentrate, a wettable powder, a dust, a granule and a tablet which can be prepared by admixing the active ingredient with a suitable inert liquid or solid carrier and another adjuvant such as suitable surfactants.

Suitable liquid carriers include benzene, alcohols, acetone, xylene, cyclohexane, methylnaphthalene, dimethylsulfoxide, dimethylformamide, animal or vegetable oils, fatty acids, fatty acid esters etc.

Suitable solid carriers include clay, kaolin clay, talc, bentonite, diatomaceous earth, silica, calcium carbonate, soybean powder, wheat powder, other plant powder etc.

It is also possible to incorporate the other agricultural chemical such as agricultural fungicides, insecticides, nematocides, and the other herbicides, plant growth regulators, soil improvers and fertilizers.

It is also possible to incorporate a suitable adjuvant such as a spreader, an emulsifier, a wet spreader and a sticker for improving the herbicidal effect.

The compound (I) as the active ingredient is usually incorporated in the herbicidal composition of the present invention at a ratio of 0.5 to 95% by weight.

Suitable amounts of the active ingredient and the adjuvants in the herbicidal compositions of the present invention are as follows.

| | Active ingredient | (% by weight) Surfactant | Carrier |
|---|---|---|---|
| Wettable powder | 5 to 80 | 1 to 20 | 0 to 85 |
| Dust | 0.5 to 30 | 0 to 5 | 99.5 to 70 |
| Granule | 0.5 to 30 | 0 to 15 | 99.5 to 55 |
| Emulsifiable concentrate | 5 to 70 | 1 to 20 | 10 to 90 |

A dose of the compound (I) as the herbicide is 1.25 to 80 g. per/are.

It is especially suitable to apply the compounds of the present invention in a form of a wettable powder.

The compounds (I) are the herbicide impart highly selective herbicidal effect in a soil treatment and a foliage treatment in up-land or paddy field to be low phytotoxicity to crop plants such as rice, wheat, corn etc., but to kill gramineous weeds and broad leaf weeds especially perennial weeds such as Narrowleaf waterplantain, Arrowhead (*Sagittaria trifolia* L.), Water chestnut, Matai (Eleocharis Kuroguwai Ohwi) which are troublesome in a culture of rice plants.

The herbicide is especially effective in an up-land soil treatment and a flooded treatment.

The herbicides and herbicidal compositions of the present invention will be further illustrated by certain examples for preparations and herbicidal experimental tests which are provided for purposes of illustration only and are not intended to be limiting the present invention.

In the preparations and the experiments, the term "part" means "part by weight" and Compound numbers correspond to Compounds shown in Table 3. As references, the following compounds are also used.

| Reference A Compound | 2,4,6-trichlorophenyl-4'-nitrophenylether; |
|---|---|
| Reference B Compound | S-(4-chlorobenzyl)-N,N-diethylthiolcarbamate; |
| Reference C Compound | 3-(3,4-dichlorophenyl)-1,1-dimethylurea; |
| Reference D Compound | 2,4-dichlorophenyl-4'-nitrophenylether; |
| Reference E Compound | N-(2,4-dichlorophenyl)-3,4,5,6-tetrahydrophthalimide; |
| Reference F Compound | N-(3-methoxy-4-chlorophenyl)-3,4,5,6-tetrahydrophthalimide; |
| Reference G Compound | N-(3-methoxy-4-bromophenyl)-3,4,5,6-tetrahydrophthalimide; |
| Reference H Compound | 3,4-dichloropropionanilide |

| Wettable powder: | |
|---|---|
| Compound shown in Table 3 | 50 parts |
| Carplex #80 (Shionogi Seiyaku K. K.) | 15 parts |
| N,N-kaolin clay (Tsuchiya Kaolin K. K.) | 30 parts |
| Sorpol 8070 (Toho Kagaku K. K.) | 5 parts |

| -continued | |
|---|---|
| Wettable powder: | |
| (higher alkyl sulfate surfactant) | |

The components were uniformly mixed and ground to obtain a wettable powder containing 50% of the active ingredient.

| Granule: | |
|---|---|
| Compound shown in Table 3 | 5 parts |
| Clay (Nippon Talc K. K.) | 38 parts |
| Bentonite (Hojunyoko K. K.) | 55 parts |
| Aerol CT-1 (Toho Kagaku K. K.) | 2 parts |
| (succinate type surfactant) | |

The components were mixed with water and kneaded and granulated by a granulating machine and dried at 60° C. for 2 hours to obtain a granule containing 5% of the active ingredient.

| Emulsifiable concentrate: | |
|---|---|
| Compound shown in Table 3 | 30 parts |
| Xylene | 30 parts |
| Dimethylformamide | 25 parts |

The compound was dissolved into the mixed solvent and then, 15 parts of polyoxyethylene type surfactant (Sorpol 3005X: Toho Kagaku K.K.) was admixed to obtain an emulsifiable concentrate containing 30% of the active ingredient.

In the tests, the following weeds were used and the weeds are shown by the following symbols.

Barnyardgrass (*Echinochloa crus-galli*): B.G.
Tooth cup (*Rotala ramasior*): T.C.
Narrowleaf waterplantain (*Alisma gramineum*): N.W.
Hardstem bulrush (*Scirpus acutus*): H.B.
Crabgrass (*Digitaria songuinalis* (L.) Scop): C.G.
Smallflower galinsoga (*Galinsoga parviflora* (av.): S.G.
Lambsguarter (*Chenopoduim album* L.): L.A.
Sawa millet (*Echinochloa crus-galli* Beauv. var. *frumentacea* Trin): S.M.
Wild amaranth (*Amaranthus lividus* L.) W.A.
Pink Persicaria (*Polygonum persicaria* L.) P.P.
Common chickweed (*Stellaria media* Vill.) C.C.
Prickly side (*Sida spinosd* L.) P.S.
Common purslane (*Portulaca oleracea* L.) C.P.

Test A:

(i) Flooded paddy field test for preemergence of paddy weeds:

Each pot of 1/2500 are filled with paddy diluvium soil and manured (fertilizer application) and seeds of Barnyardgrass, Tooth cup, Hardstem bulrush, and Narrowleaf waterplantain were sown. The seeds were mixed well in the upper layer having a thickness of 2 cm and the pot was flooded in a depth of about 3 cm. Next day, each wettable powder containing each of Compounds No. 1 to 27 and Reference Compunds A and B as the active ingredient was diluted with water and the diluted solution was applied so as to give each dose of the active ingredient by a drop treatment under the flooded surface.

For two days after the treatment, a leaching loss of water was given at a rate of 3 cm/day and the pot was kept in a greenhouse.

Twenty one days after the treatment, survival quantities of the plants were measured to find herbicidal effects to weeds. The results are shown in Table 4. Herbicidal effects are rated by the following equation and ratings.

$$\left(1 - \frac{\text{Survival terrestrial weed weight in treated pot}}{\text{Survival terrestrial weed in non-treated pot}}\right) \times 100 = Y\,(\%)$$

| Herbicidal effect rating | Y (%) |
| --- | --- |
| 0 | 0–4 |
| 1 | 5–29 |
| 2 | 30–49 |
| 3 | 50–69 |
| 4 | 70–89 |
| 5 | 90–100 |

TABLE 4

| Compound No. | Dose of active ingredient (g/a) | Herbicidal Effect B.G. | T.C. | N.W. | H.B. |
| --- | --- | --- | --- | --- | --- |
| 1 | 20 | 5 | 5 | 5 | 5 |
|  | 10 | 5 | 5 | 5 | 5 |
|  | 5 | 5 | 5 | 5 | 5 |
| 2 | 20 | 5 | 5 | 5 | 5 |
|  | 10 | 5 | 5 | 5 | 5 |
|  | 5 | 5 | 5 | 5 | 5 |
| 3 | 20 | 5 | 5 | 5 | 5 |
|  | 10 | 5 | 5 | 5 | 5 |
|  | 5 | 5 | 5 | 5 | 5 |
| 4 | 20 | 5 | 5 | 5 | 5 |
|  | 10 | 5 | 5 | 5 | 5 |
|  | 5 | 5 | 5 | 5 | 5 |
| 5 | 20 | 5 | 5 | 5 | 5 |
|  | 10 | 5 | 5 | 5 | 5 |
|  | 5 | 5 | 5 | 5 | 5 |
| 6 | 20 | 5 | 5 | 5 | 5 |
|  | 10 | 5 | 5 | 5 | 5 |
|  | 5 | 5 | 5 | 5 | 5 |
| 7 | 20 | 5 | 5 | 5 | 5 |
|  | 10 | 5 | 5 | 5 | 5 |
|  | 5 | 5 | 5 | 5 | 4 |
| 8 | 20 | 5 | 5 | 5 | 5 |
|  | 10 | 5 | 5 | 5 | 5 |
|  | 5 | 5 | 5 | 5 | 4 |
| 9 | 20 | 5 | 5 | 5 | 5 |
|  | 10 | 5 | 5 | 5 | 4 |
|  | 5 | 5 | 5 | 5 | 4 |
| 10 | 20 | 5 | 5 | 5 | 5 |
|  | 10 | 5 | 5 | 5 | 4 |
|  | 5 | 4 | 5 | 5 | 3 |
| 11 | 20 | 5 | 5 | 5 | 5 |
|  | 10 | 5 | 5 | 5 | 4 |
|  | 5 | 5 | 5 | 5 | 4 |
| 12 | 40 | 5 | 5 | 5 | 4 |
|  | 20 | 4 | 5 | 4 | 4 |
|  | 10 | 3 | 4 | 4 | 3 |
| 13 | 40 | 5 | 5 | 5 | 5 |
|  | 20 | 4 | 5 | 5 | 4 |
|  | 10 | 4 | 5 | 5 | 3 |
| 14 | 80 | 5 | 5 | 5 | 4 |
|  | 40 | 4 | 5 | 4 | 4 |
|  | 20 | 3 | 4 | 3 | 3 |
| 15 | 20 | 5 | 5 | 5 | 5 |
|  | 10 | 5 | 5 | 5 | 4 |
|  | 5 | 5 | 5 | 5 | 4 |
| 16 | 40 | 5 | 5 | 5 | 5 |
|  | 20 | 5 | 5 | 5 | 4 |
|  | 10 | 5 | 5 | 4 | 4 |
| 17 | 40 | 5 | 5 | 5 | 5 |
|  | 20 | 5 | 5 | 5 | 5 |

TABLE 4-continued

| Compound No. | Dose of active ingredient (g/a) | Herbicidal Effect B.G. | T.C. | N.W. | H.B. |
| --- | --- | --- | --- | --- | --- |
|  | 10 | 5 | 5 | 5 | 4 |
|  | 40 | 5 | 5 | 5 | 5 |
| 18 | 20 | 5 | 5 | 5 | 4 |
|  | 10 | 5 | 5 | 4 | 4 |
|  | 80 | 5 | 5 | 5 | 4 |
| 19 | 40 | 4 | 5 | 4 | 4 |
|  | 20 | 4 | 4 | 4 | 3 |
|  | 20 | 5 | 5 | 5 | 5 |
| 20 | 10 | 5 | 5 | 5 | 5 |
|  | 5 | 5 | 5 | 5 | 4 |
|  | 40 | 5 | 5 | 5 | 5 |
| 21 | 20 | 5 | 5 | 5 | 4 |
|  | 10 | 4 | 5 | 5 | 4 |
|  | 40 | 5 | 5 | 5 | 5 |
| 22 | 20 | 5 | 5 | 5 | 5 |
|  | 10 | 5 | 5 | 5 | 5 |
|  | 40 | 5 | 5 | 5 | 5 |
| 23 | 20 | 5 | 5 | 5 | 5 |
|  | 10 | 5 | 5 | 5 | 4 |
|  | 40 | 5 | 5 | 5 | 5 |
| 24 | 20 | 5 | 5 | 5 | 4 |
|  | 10 | 4 | 5 | 5 | 4 |
|  | 80 | 5 | 5 | 5 | 4 |
| 25 | 40 | 4 | 5 | 5 | 3 |
|  | 20 | 3 | 5 | 4 | 3 |
|  | 80 | 4 | 5 | 5 | 4 |
| 26 | 40 | 4 | 5 | 4 | 3 |
|  | 20 | 3 | 5 | 4 | 3 |
|  | 80 | 5 | 5 | 5 | 4 |
| 27 | 40 | 4 | 5 | 5 | 4 |
|  | 20 | 4 | 5 | 4 | 4 |
|  | 40 | 5 | 5 | 5 | 5 |
| 28 | 20 | 5 | 5 | 5 | 5 |
|  | 10 | 5 | 5 | 5 | 3 |
|  | 40 | 5 | 5 | 5 | 5 |
| 29 | 20 | 5 | 5 | 5 | 5 |
|  | 10 | 5 | 5 | 5 | 5 |
|  | 40 | 5 | 5 | 5 | 5 |
| 30 | 20 | 5 | 5 | 5 | 5 |
|  | 10 | 5 | 5 | 5 | 4 |
|  | 20 | 5 | 5 | 2 | 2 |
| Reference A | 10 | 4 | 5 | 1 | 0 |
|  | 5 | 2 | 4 | 0 | 0 |
|  | 20 | 5 | 5 | 3 | 3 |
| Reference B | 10 | 5 | 5 | 1 | 0 |
|  | 5 | 3 | 3 | 0 | 0 |
| Non-treatment | — | 0 | 0 | 0 | 0 |

Test B

In accordance with the experiment of Test A, each test was carried out by using Compounds No. 31 to 53 and Reference Compounds A, E and F. The results are shown in Table 5. The ratings are the same as those of Test A.

TABLE 5

| Compound No. | Dose of active ingredient (g/a) | Herbicidal Effect B.G. | T.C. | N.W. | H.B. |
| --- | --- | --- | --- | --- | --- |
|  | 20 | 5 | 5 | 5 | 5 |
| 31 | 10 | 5 | 5 | 5 | 5 |
|  | 5 | 5 | 5 | 5 | 5 |
|  | 20 | 5 | 5 | 5 | 5 |
| 32 | 10 | 5 | 5 | 5 | 5 |
|  | 5 | 5 | 5 | 5 | 5 |
|  | 20 | 5 | 5 | 5 | 5 |
| 33 | 10 | 5 | 5 | 5 | 5 |
|  | 5 | 5 | 5 | 5 | 5 |
|  | 20 | 5 | 5 | 5 | 5 |
| 34 | 10 | 5 | 5 | 5 | 5 |
|  | 5 | 5 | 5 | 5 | 5 |
|  | 20 | 5 | 5 | 5 | 5 |

TABLE 5-continued

| Compound No. | Dose of active ingredient (g/a) | Herbicidal Effect B.G. | T.C. | N.W. | H.B. |
| --- | --- | --- | --- | --- | --- |
| 35 | 10 | 5 | 5 | 5 | 5 |
|  | 5 | 5 | 5 | 5 | 5 |
|  | 20 | 5 | 5 | 5 | 5 |
| 36 | 10 | 5 | 5 | 5 | 5 |
|  | 5 | 5 | 5 | 5 | 5 |
|  | 20 | 5 | 5 | 5 | 5 |
| 37 | 10 | 5 | 5 | 5 | 5 |
|  | 5 | 5 | 5 | 5 | 5 |
|  | 20 | 5 | 5 | 5 | 5 |
| 38 | 10 | 5 | 5 | 5 | 5 |
|  | 5 | 5 | 5 | 5 | 5 |
|  | 20 | 5 | 5 | 5 | 5 |
| 39 | 10 | 5 | 5 | 5 | 5 |
|  | 5 | 5 | 5 | 5 | 5 |
|  | 20 | 5 | 5 | 5 | 5 |
| 40 | 10 | 5 | 5 | 5 | 5 |
|  | 5 | 5 | 5 | 5 | 5 |
|  | 20 | 5 | 5 | 5 | 5 |
| 41 | 10 | 5 | 5 | 5 | 5 |
|  | 5 | 5 | 5 | 5 | 5 |
|  | 20 | 5 | 5 | 5 | 5 |
| 42 | 10 | 5 | 5 | 5 | 4 |
|  | 5 | 4 | 5 | 5 | 3 |
|  | 20 | 5 | 5 | 5 | 5 |
| 43 | 10 | 5 | 5 | 5 | 5 |
|  | 5 | 5 | 5 | 5 | 4 |
|  | 20 | 5 | 5 | 5 | 5 |
| 44 | 10 | 5 | 5 | 5 | 4 |
|  | 5 | 5 | 5 | 5 | 4 |
|  | 20 | 5 | 5 | 5 | 5 |
| 45 | 10 | 5 | 5 | 5 | 5 |
|  | 5 | 5 | 5 | 5 | 5 |
|  | 20 | 5 | 5 | 5 | 5 |
| 46 | 10 | 5 | 5 | 5 | 5 |
|  | 5 | 5 | 5 | 5 | 4 |
|  | 20 | 5 | 5 | 5 | 5 |
| 47 | 10 | 5 | 5 | 5 | 4 |
|  | 5 | 5 | 5 | 5 | 4 |
|  | 40 | 5 | 5 | 5 | 4 |
| 48 | 20 | 4 | 5 | 4 | 4 |
|  | 10 | 4 | 4 | 3 | 3 |
|  | 20 | 5 | 5 | 5 | 5 |
| 49 | 10 | 5 | 5 | 5 | 5 |
|  | 5 | 5 | 5 | 5 | 4 |
|  | 20 | 5 | 5 | 5 | 5 |
| 50 | 10 | 5 | 5 | 5 | 4 |
|  | 5 | 5 | 5 | 5 | 4 |
|  | 20 | 5 | 5 | 5 | 5 |
| 51 | 10 | 5 | 5 | 5 | 5 |
|  | 5 | 5 | 5 | 5 | 5 |
|  | 20 | 5 | 5 | 5 | 5 |
| 52 | 10 | 5 | 5 | 5 | 5 |
|  | 5 | 5 | 5 | 5 | 4 |
|  | 20 | 5 | 5 | 5 | 5 |
| 53 | 10 | 5 | 5 | 5 | 4 |
|  | 5 | 4 | 5 | 5 | 4 |
|  | 40 | 5 | 5 | 5 | 4 |
| Reference E | 20 | 4 | 5 | 5 | 4 |
|  | 10 | 3 | 4 | 3 | 3 |
|  | 40 | 5 | 5 | 5 | 5 |
| Reference F | 20 | 5 | 4 | 4 | 4 |
|  | 10 | 3 | 4 | 3 | 2 |
|  | 20 | 5 | 5 | 3 | 2 |
| Reference A | 10 | 4 | 4 | 1 | 0 |
|  | 5 | 2 | 4 | 0 | 0 |
| Non-treatment | — | 0 | 0 | 0 | 0 |

Test C:

Phytotoxicity test for rice seedlings:

Each Wagner pot of 1/5,000 was filled with paddy diluvium soil and manured (fertilizer application) and puddled with suitable water and two rice seedlings of 2.5 leaf stage (Kinmaze, height of 13.5 cm: good seedling) were transplanted in a depth of about 2 cm, and the pot was flooded in a depth of 3.5 cm.

Zero or seven days after the transplantation, each granule containing each of Compounds No. 1 to 9 and 20 to 29 and Reference Compound A and B was fallen on the flooded surface at each dose of the compound shown in Table 6.

For two days after the treatment, a leaching loss of water was given at a rate of 3 cm/day and the pot was kept in greehouse.

Twenty one days after the treatment, phytotoxicities of the compounds to rice seedlings were observed. The results are shown in Table 6.

| Rating | Damage |
| --- | --- |
| 0 | non-damage |
| 1 | slight damage |
| 2 | fair damage |
| 3 | middle damage |
| 4 | serious damage |
| 5 | death |

TABLE 6

| Compound No. | Dose of active ingredient (g/a) | Phytotoxicity to rice seedling same day transplantation | 7 days after transplantation |
| --- | --- | --- | --- |
| 1 | 40 | 2 | 2 |
|  | 20 | 1 | 0 |
|  | 10 | 0 | 0 |
| 2 | 40 | 2 | 1 |
|  | 20 | 0 | 0 |
|  | 10 | 0 | 0 |
| 3 | 40 | 1 | 0 |
|  | 20 | 1 | 0 |
|  | 10 | 0 | 0 |
| 4 | 40 | 2 | 2 |
|  | 20 | 1 | 0 |
|  | 10 | 0 | 0 |
| 5 | 40 | 2 | 1 |
|  | 20 | 1 | 0 |
|  | 10 | 0 | 0 |
| 6 | 40 | 1 | 0 |
|  | 20 | 0 | 0 |
|  | 10 | 0 | 0 |
| 7 | 40 | 2 | 0 |
|  | 20 | 0 | 0 |
|  | 10 | 0 | 0 |
| 8 | 40 | 1 | 0 |
|  | 20 | 0 | 0 |
|  | 10 | 0 | 0 |
| 9 | 40 | 1 | 0 |
|  | 20 | 0 | 0 |
|  | 10 | 0 | 0 |
| 20 | 40 | 1 | 0 |
|  | 20 | 0 | 0 |
|  | 10 | 0 | 0 |
| 21 | 40 | 0 | 0 |
|  | 20 | 0 | 0 |
|  | 10 | 0 | 0 |
| 22 | 40 | 0 | 0 |
|  | 20 | 0 | 0 |
|  | 10 | 0 | 0 |
| 23 | 40 | 1 | 0 |
|  | 20 | 0 | 0 |
|  | 10 | 0 | 0 |
| 24 | 40 | 0 | 0 |
|  | 20 | 0 | 0 |
|  | 10 | 0 | 0 |
| 25 | 40 | 0 | 0 |
|  | 20 | 0 | 0 |
|  | 10 | 0 | 0 |
| 26 | 40 | 0 | 0 |
|  | 20 | 0 | 0 |
|  | 10 | 0 | 0 |
| 27 | 40 | 0 | 0 |
|  | 20 | 0 | 0 |

TABLE 6-continued

| Compound No. | Dose of active ingredient (g/a) | Phytotoxicity to rice seedling same day transplantation | 7 days after transplantation |
|---|---|---|---|
|  | 10 | 0 | 0 |
|  | 40 | 0 | 0 |
| 28 | 20 | 0 | 0 |
|  | 10 | 0 | 0 |
|  | 40 | 1 | 0 |
| 29 | 20 | 0 | 0 |
|  | 10 | 0 | 0 |
|  | 40 | 1 | 0 |
| 30 | 20 | 0 | 0 |
|  | 10 | 0 | 0 |
|  | 40 | 2 | 1 |
| Reference A | 20 | 1 | 0 |
|  | 10 | 0 | 0 |
|  | 40 | 3-4 | 3 |
| Reference B | 20 | 2 | 1 |
|  | 10 | 0 | 0 |
| Non-treatment | — | 0 | 0 |

Test D

In accordance with the experiment of Test C, except transplanting two rice seedlings of 2.7 leaf stage (Nihonbare, height of 15.5 cm; slightly good) in each pot, each phytotoxicity of each of Compounds No. 1 to 5 and 15 to 20 and Reference Compounds A, B, E and F was tested and rated. The results are shown in Table 7.

TABLE 7

| Compound No. | Dose of active ingredient (g/a) | Phytotoxicity to rice seedling one day after transplantation | 7 days after transplantation |
|---|---|---|---|
|  | 40 | 3 | 1 |
| 31 | 20 | 0 | 0 |
|  | 10 | 0 | 0 |
|  | 40 | 2 | 2 |
| 32 | 20 | 1 | 0 |
|  | 10 | 0 | 0 |
|  | 40 | 2 | 0 |
| 33 | 20 | 0 | 0 |
|  | 10 | 0 | 0 |
|  | 40 | 2 | 1 |
| 34 | 20 | 1 | 0 |
|  | 10 | 0 | 0 |
|  | 40 | 2 | 1 |
| 35 | 20 | 2 | 0 |
|  | 10 | 0 | 0 |
|  | 40 | 2 | 1 |
| 45 | 20 | 0 | 0 |
|  | 10 | 0 | 0 |
|  | 40 | 2 | 1 |
| 46 | 20 | 0 | 0 |
|  | 10 | 0 | 0 |
|  | 40 | 1 | 0 |
| 47 | 20 | 0 | 0 |
|  | 10 | 0 | 0 |
|  | 40 | 0 | 0 |
| 48 | 20 | 0 | 0 |
|  | 10 | 0 | 0 |
|  | 40 | 2 | 0 |
| 49 | 20 | 0 | 0 |
|  | 10 | 0 | 0 |
|  | 40 | 1 | 0 |
| 50 | 20 | 0 | 0 |
|  | 10 | 0 | 0 |
|  | 40 | 2 | 1 |
| Reference E | 20 | 0 | 0 |
|  | 10 | 0 | 0 |
|  | 40 | 2 | 1 |
| Reference F | 20 | 1 | 0 |
|  | 10 | 0 | 0 |
|  | 40 | 3 | 1 |
| Reference A | 20 | 1 | 0 |
|  | 10 | 0 | 0 |

TABLE 7-continued

| Compound No. | Dose of active ingredient (g/a) | Phytotoxicity to rice seedling one day after transplantation | 7 days after transplantation |
|---|---|---|---|
|  | 40 | 4 | 3 |
| Reference B | 20 | 2 | 1 |
|  | 10 | 0 | 0 |
| Non-treatment | — | 0 | 0 |

Test E

Up-land soil treatment test:

Each plastic pot of ½, 500 are was filled with black volcano ash soil and manured and seeds of wheat, soybean, corn and cotton were sown and were covered with the soil in a depth of 2 to 3 cm and seeds of weeds of Crabgrass and Smallflower galinsoga were mixed in the covered soil layer. Each wettable powder containing each of Compounds No. 1 to 13 and 20 to 22 and Reference Compounds C and D was diluted with water and the solution was sprayed uniformly on the surface of the soil at a dose of the compound shown in Table 7 by a small size power pressurized spray.

Twenty days after the treatment, herbicidal effects were observed and phytotoxicities to the crop plants were also observed. The results are shown in Table 8.

The herbicidal effects are rated as those of Test A and the phytotoxicities to crop plants are rated as those of Test C.

TABLE 8

| Comp. No. | Dose of Comp. (g/a) | Herbicidal effect C.G. | Herbicidal effect S.G. | Phytotoxicity to crop plants Wheat | Soybean | Corn | Cotton |
|---|---|---|---|---|---|---|---|
|  | 40 | 5 | 5 | 2 | 0 | 0 | 0 |
| 1 | 20 | 5 | 5 | 0 | 0 | 0 | 0 |
|  | 10 | 5 | 5 | 0 | 0 | 0 | 0 |
|  | 40 | 5 | 5 | 1 | 0 | 0 | 0 |
| 2 | 20 | 5 | 5 | 0 | 0 | 0 | 0 |
|  | 10 | 5 | 5 | 0 | 0 | 0 | 0 |
|  | 40 | 5 | 5 | 1 | 0 | 0 | 1 |
| 3 | 20 | 5 | 5 | 0 | 0 | 0 | 0 |
|  | 10 | 5 | 5 | 0 | 0 | 0 | 0 |
|  | 40 | 5 | 5 | 2 | 1 | 0 | 1 |
| 4 | 20 | 5 | 5 | 0 | 0 | 0 | 0 |
|  | 10 | 5 | 5 | 0 | 0 | 0 | 0 |
|  | 40 | 5 | 5 | 1 | 0 | 0 | 0 |
| 5 | 20 | 5 | 5 | 0 | 0 | 0 | 0 |
|  | 10 | 5 | 5 | 0 | 0 | 0 | 0 |
|  | 40 | 5 | 5 | 1 | 0 | 0 | 0 |
| 6 | 20 | 5 | 5 | 0 | 0 | 0 | 0 |
|  | 10 | 5 | 5 | 0 | 0 | 0 | 0 |
|  | 40 | 5 | 5 | 0 | 0 | 0 | 0 |
| 7 | 20 | 5 | 5 | 0 | 0 | 0 | 0 |
|  | 10 | 4 | 5 | 0 | 0 | 0 | 0 |
|  | 40 | 5 | 5 | 0 | 0 | 0 | 0 |
| 8 | 20 | 5 | 5 | 0 | 0 | 0 | 0 |
|  | 10 | 4 | 4 | 0 | 0 | 0 | 0 |
|  | 40 | 5 | 5 | 0 | 0 | 0 | 0 |
| 9 | 20 | 4 | 5 | 0 | 0 | 0 | 0 |
|  | 10 | 4 | 4 | 0 | 0 | 0 | 0 |
|  | 80 | 4 | 5 | 0 | 0 | 0 | 0 |
| 10 | 40 | 4 | 4 | 0 | 0 | 0 | 0 |
|  | 20 | 3 | 4 | 0 | 0 | 0 | 0 |
|  | 80 | 5 | 5 | 0 | 0 | 0 | 0 |
| 11 | 40 | 4 | 4 | 0 | 0 | 0 | 0 |
|  | 20 | 3 | 4 | 0 | 0 | 0 | 0 |
|  | 80 | 4 | 4 | 0 | 0 | 0 | 0 |
| 12 | 40 | 4 | 4 | 0 | 0 | 0 | 0 |
|  | 20 | 3 | 3 | 0 | 0 | 0 | 0 |
|  | 80 | 4 | 5 | 0 | 0 | 0 | 0 |
| 13 | 40 | 4 | 3 | 0 | 0 | 0 | 0 |
|  | 20 | 3 | 3 | 0 | 0 | 0 | 0 |
|  | 80 | 5 | 5 | 2 | 0 | 0 | 0 |
| 20 | 40 | 5 | 5 | 0 | 0 | 0 | 0 |

TABLE 8-continued

| Comp. No. | Dose of Comp. (g/a) | Herbicidal effect C.G. | Herbicidal effect S.G. | Phytotoxicity to crop plants Wheat | Soybean | Corn | Cotton |
| --- | --- | --- | --- | --- | --- | --- | --- |
| | 20 | 4 | 5 | 0 | 0 | 0 | 0 |
| | 80 | 4 | 5 | 0 | 0 | 0 | 0 |
| 21 | 40 | 4 | 4 | 0 | 0 | 0 | 0 |
| | 20 | 3 | 3 | 0 | 0 | 0 | 0 |
| | 40 | 5 | 5 | 0 | 0 | 0 | 0 |
| 22 | 20 | 4 | 5 | 0 | 0 | 0 | 0 |
| | 10 | 3 | 4 | 0 | 0 | 0 | 0 |
| | 40 | 5 | 5 | 2 | 0 | 0 | 1 |
| 27 | 20 | 5 | 5 | 1 | 0 | 0 | 0 |
| | 10 | 5 | 5 | 0 | 0 | 0 | 0 |
| | 40 | 5 | 5 | 2 | 0 | 0 | 1 |
| 29 | 20 | 5 | 5 | 0 | 0 | 0 | 0 |
| | 10 | 5 | 5 | 0 | 0 | 0 | 0 |
| | 40 | 5 | 5 | 4 | 3 | 1 | 2 |
| Ref. C | 20 | 5 | 5 | 2 | 1 | 0 | 0 |
| | 10 | 3 | 5 | 0 | 0 | 0 | 0 |
| | 40 | 5 | 5 | 3 | 1 | 0 | 0 |
| Ref. D | 20 | 4 | 5 | 1 | 0 | 0 | 0 |
| | 10 | 2 | 4 | 0 | 0 | 0 | 0 |
| Non-treatment | — | 0 | 0 | 0 | 0 | 0 | 0 |

Test F

In accordance with the experiment of Test E, except mixing seeds of Crabgrass, Smallflower galinsoga and Lambsquarter in the covered soil layer after sowing seeds of wheat, soybean, corn and cotton, each phytotoxicity and herbicidal effect of each of Compounds No. 31 to 45 and Reference Compounds F, G, C and D were tested. The results are shown in Table 9.

TABLE 9

| Comp. No. | Dose of Comp. (g/a) | Herbicidal effect C.G. | Herbicidal effect S.G. | Herbicidal effect L.A. | Phytotoxicity to crop plants Wheat | Soybean | Corn | Cotton |
| --- | --- | --- | --- | --- | --- | --- | --- | --- |
| | 40 | 5 | 5 | 5 | 2 | 0 | 0 | 1 |
| 31 | 20 | 5 | 5 | 5 | 0 | 0 | 0 | 0 |
| | 10 | 5 | 5 | 5 | 0 | 0 | 0 | 0 |
| | 40 | 5 | 5 | 5 | 1 | 0 | 0 | 1 |
| 32 | 20 | 5 | 5 | 5 | 0 | 0 | 0 | 0 |
| | 10 | 5 | 4 | 5 | 0 | 0 | 0 | 0 |
| | 40 | 5 | 5 | 5 | 0 | 0 | 0 | 0 |
| 33 | 20 | 5 | 5 | 5 | 0 | 0 | 0 | 0 |
| | 10 | 4 | 4 | 5 | 0 | 0 | 0 | 0 |
| | 40 | 5 | 5 | 5 | 1 | 0 | 0 | 0 |
| 34 | 20 | 5 | 5 | 5 | 0 | 0 | 0 | 0 |
| | 10 | 5 | 5 | 5 | 0 | 0 | 0 | 0 |
| | 40 | 5 | 5 | 5 | 2 | 0 | 0 | 0 |
| 35 | 20 | 5 | 5 | 5 | 0 | 0 | 0 | 0 |
| | 10 | 5 | 4 | 4 | 0 | 0 | 0 | 0 |
| | 40 | 5 | 5 | 5 | 1 | 0 | 0 | 0 |
| 36 | 20 | 5 | 5 | 5 | 0 | 0 | 0 | 0 |
| | 10 | 5 | 5 | 5 | 0 | 0 | 0 | 0 |
| | 40 | 5 | 5 | 5 | 1 | 0 | 0 | 1 |
| 37 | 20 | 5 | 5 | 5 | 0 | 0 | 0 | 0 |
| | 10 | 5 | 5 | 5 | 0 | 0 | 0 | 0 |
| | 40 | 5 | 5 | 5 | 1 | 0 | 0 | 0 |
| 38 | 20 | 5 | 5 | 5 | 0 | 0 | 0 | 0 |
| | 10 | 5 | 5 | 5 | 0 | 0 | 0 | 0 |
| | 40 | 5 | 5 | 5 | 0 | 0 | 0 | 0 |
| 39 | 20 | 5 | 4 | 5 | 0 | 0 | 0 | 0 |
| | 10 | 5 | 5 | 5 | 0 | 0 | 0 | 0 |
| | 40 | 5 | 5 | 5 | 1 | 0 | 0 | 0 |
| 40 | 20 | 5 | 4 | 5 | 0 | 0 | 0 | 0 |
| | 10 | 5 | 5 | 5 | 0 | 0 | 0 | 0 |
| | 40 | 5 | 5 | 5 | 0 | 0 | 0 | 0 |
| 41 | 20 | 5 | 5 | 5 | 0 | 0 | 0 | 0 |
| | 10 | 5 | 4 | 4 | 0 | 0 | 0 | 0 |
| | 80 | 5 | 4 | 5 | 0 | 0 | 0 | 0 |
| 42 | 40 | 4 | 4 | 5 | 0 | 0 | 0 | 0 |
| | 20 | 3 | 3 | 3 | 0 | 0 | 0 | 0 |

TABLE 9-continued

| Comp. No. | Dose of Comp. (g/a) | Herbicidal effect C.G. | Herbicidal effect S.G. | Herbicidal effect L.A. | Phytotoxicity to crop plants Wheat | Soybean | Corn | Cotton |
| --- | --- | --- | --- | --- | --- | --- | --- | --- |
| | 40 | 5 | 5 | 5 | 1 | 0 | 0 | 1 |
| 43 | 20 | 5 | 5 | 5 | 0 | 0 | 0 | 0 |
| | 10 | 5 | 4 | 5 | 0 | 0 | 0 | 0 |
| | 80 | 5 | 5 | 5 | 0 | 0 | 0 | 0 |
| 44 | 40 | 4 | 3 | 5 | 0 | 0 | 0 | 0 |
| | 20 | 3 | 3 | 3 | 0 | 0 | 0 | 0 |
| | 40 | 5 | 5 | 5 | 1 | 0 | 0 | 0 |
| 45 | 20 | 5 | 5 | 5 | 0 | 0 | 0 | 0 |
| | 10 | 5 | 4 | 5 | 0 | 0 | 0 | 0 |
| | 40 | 5 | 5 | 5 | 1 | 0 | 0 | 0 |
| Ref. F | 20 | 4 | 4 | 4 | 0 | 0 | 0 | 0 |
| | 10 | 3 | 3 | 3 | 0 | 0 | 0 | 0 |
| | 40 | 5 | 5 | 5 | 2 | 0 | 0 | 0 |
| Ref. G | 20 | 4 | 5 | 4 | 0 | 0 | 0 | 0 |
| | 10 | 3 | 3 | 4 | 0 | 0 | 0 | 0 |
| | 40 | 5 | 5 | 5 | 4 | 3 | 1 | 2 |
| Ref. C | 20 | 5 | 5 | 5 | 1 | 1 | 0 | 0 |
| | 10 | 3 | 4 | 3 | 0 | 0 | 0 | 0 |
| | 40 | 5 | 5 | 5 | 3 | 1 | 0 | 1 |
| Ref. D | 20 | 4 | 4 | 4 | 1 | 0 | 0 | 0 |
| | 10 | 2 | 4 | 3 | 0 | 0 | 0 | 0 |
| Non-treatment | — | 0 | 0 | 0 | 0 | 0 | 0 | 0 |

Test G

Foliage treatment test:

Each polyethylene pot was filled with black volcano ash soil and manured and seeds of Sawa millet, Crabgrass and Radish were respectively sown in each pot. The pot was kept in a greenhouse. When Sawa millet and Crabgrass were grown to 2 to 3 leaf stage and Radish to 1 leaf stage, each solution prepared by diluting each emulsifiable concentrate containing each of Compounds No. 1 to 9 and Reference Compounds H, at a concentration of 0.5, 0.25 or 0.125%, was sprayed at a rate of 10 liter per are by a small power pressurized sprayer and the pot in the greenhouse was observed.

Fifteen days after the treatment, herbicidal effects were observed. The results are shown in Table 10.

The herbicidal effects are rated as those of Test A.

TABLE 10

| Compound No. | Concentration % | Herbicidal effect S.M. | C.G. | Radish |
| --- | --- | --- | --- | --- |
| | 0.5 | 5 | 5 | 5 |
| 1 | 0.25 | 4 | 5 | 5 |
| | 0.125 | 4 | 4 | 4 |
| | 0.5 | 5 | 5 | 5 |
| 2 | 0.25 | 5 | 5 | 5 |
| | 0.125 | 3 | 5 | 4 |
| | 0.5 | 5 | 5 | 5 |
| 3 | 0.25 | 4 | 5 | 4 |
| | 0.125 | 4 | 4 | 4 |
| | 0.5 | 5 | 5 | 5 |
| 4 | 0.25 | 5 | 5 | 5 |
| | 0.125 | 5 | 5 | 5 |
| | 0.5 | 5 | 5 | 5 |
| 5 | 0.25 | 5 | 4 | 5 |
| | 0.125 | 3 | 4 | 4 |
| | 0.5 | 5 | 5 | 5 |
| 6 | 0.25 | 5 | 5 | 5 |
| | 0.125 | 5 | 5 | 5 |
| | 0.5 | 5 | 5 | 5 |
| 7 | 0.25 | 4 | 4 | 4 |
| | 0.125 | 4 | 4 | 3 |
| | 0.5 | 5 | 5 | 5 |
| 8 | 0.25 | 4 | 4 | 4 |
| | 0.125 | 3 | 4 | 3 |
| | 0.5 | 5 | 5 | 5 |

TABLE 10-continued

| Compound No. | Concentration % | Herbicidal effect S.M. | C.G. | Radish |
|---|---|---|---|---|
| 9 | 0.25 | 5 | 4 | 4 |
|  | 0.125 | 4 | 4 | 4 |
|  | 0.5 | 5 | 5 | 4 |
| Reference H | 0.25 | 4 | 5 | 4 |
|  | 0.125 | 3 | 4 | 3 |
| Non-treatment | — | 0 | 0 | 0 |

Test H

In accordance with the experiment of Test G, each herbicidal effect of each of Compounds No. 31 to 40 and Reference Compounds F, G and H was tested. The results are shown in Table 11.

TABLE 11

| Compound No. | Concentration % | Herbicidal effect S.M. | C.G. | Radish |
|---|---|---|---|---|
|  | 0.5 | 5 | 5 | 5 |
| 31 | 0.25 | 5 | 5 | 5 |
|  | 0.125 | 3 | 4 | 4 |
|  | 0.5 | 5 | 5 | 5 |
| 32 | 0.25 | 5 | 5 | 4 |
|  | 0.125 | 4 | 4 | 4 |
|  | 0.5 | 5 | 4 | 5 |
| 33 | 0.25 | 4 | 4 | 4 |
|  | 0.125 | 3 | 4 | 4 |
|  | 0.5 | 5 | 5 | 5 |
| 34 | 0.25 | 5 | 5 | 5 |
|  | 0.125 | 4 | 5 | 4 |
|  | 0.5 | 5 | 5 | 5 |
| 35 | 0.25 | 5 | 5 | 5 |
|  | 0.125 | 5 | 5 | 5 |
|  | 0.5 | 5 | 5 | 5 |
| 36 | 0.25 | 4 | 5 | 5 |
|  | 0.125 | 4 | 4 | 5 |
|  | 0.5 | 5 | 5 | 5 |
| 37 | 0.25 | 4 | 5 | 5 |
|  | 0.125 | 4 | 4 | 5 |
|  | 0.5 | 5 | 5 | 5 |
| 38 | 0.25 | 5 | 5 | 5 |
|  | 0.125 | 3 | 4 | 5 |
|  | 0.5 | 4 | 5 | 4 |
| 39 | 0.25 | 3 | 4 | 4 |
|  | 0.125 | 3 | 3 | 3 |

TABLE 11-continued

| Compound No. | Concentration % | Herbicidal effect S.M. | C.G. | Radish |
|---|---|---|---|---|
|  | 0.5 | 5 | 5 | 5 |
| 40 | 0.25 | 5 | 5 | 5 |
|  | 0.125 | 4 | 5 | 4 |

| Compound No. | Concentration % | Herbicidal effect S.M. | C.G. | Radish |
|---|---|---|---|---|
|  | 0.5 | 5 | 5 | 5 |
| Reference F | 0.25 | 3 | 4 | 4 |
|  | 0.125 | 1 | 2 | 2 |
|  | 0.5 | 5 | 4 | 5 |
| Reference G | 0.25 | 3 | 4 | 4 |
|  | 0.125 | 2 | 2 | 3 |
|  | 0.5 | 5 | 5 | 4 |
| Reference H | 0.25 | 4 | 5 | 4 |
|  | 0.125 | 3 | 3 | 3 |
| Non-treatment | — | 0 | 0 | 0 |

Test I

Up-land soil treatment test (low dose):

Each plastic pot of ½, 500 are was filled with black volcano ash soil and manured and seeds of corn and soybean were sown and covered with the soil in a depth of 2 to 3 cm and seeds of broad leaf weeds of Wild amaranth, Common purslane, *Pink persicaria*, Lambsguarter, Smallflower, Common chickweed and Prickly sida.

Each wettable powder containing each of Compound No. 34, 37, 38, 4, 5 and 6 and Reference Compound F and G was diluted with water and the solution was sprayed uniformly on the surface of the soil at a dose of the compound shown in Table 12 by a small size power pressurized spray.

Thirty days after the treatment, herbicidal effects were observed and phytotoxicities to the crop plants were also observed. The results are shown in Table 12.

The herbicidal effects are rated as those of Test A and the phytotoxicities to crop plants are rated as those of Test C.

TABLE 12

| Comp. No. | Dose of Comp. (g/a) | Herbicidal effect W.A. | C.P. | P.P. | L.A. | S.G. | C.C. | P.S. | Phytotoxicity to crop plants Corn | Soybean |
|---|---|---|---|---|---|---|---|---|---|---|
|  | 20 | 5 | 5 | 5 | 5 | 5 | 5 | 5 | 0 | 0 |
| 34 | 10 | 5 | 5 | 5 | 5 | 5 | 5 | 5 | 0 | 0 |
|  | 5 | 5 | 5 | 5 | 5 | 5 | 4 | 5 | 0 | 0 |
|  | 2.5 | 4 | 5 | 4 | 5 | 3 | 4 | 4 | 0 | 0 |
|  | 10 | 5 | 5 | 5 | 5 | 5 | 5 | 5 | 0 | 0 |
| 37 | 5 | 5 | 5 | 5 | 5 | 5 | 5 | 5 | 0 | 0 |
|  | 2.5 | 5 | 5 | 5 | 5 | 5 | 5 | 5 | 0 | 0 |
|  | 1.25 | 5 | 5 | 4 | 5 | 4 | 4 | 5 | 0 | 0 |
|  | 20 | 5 | 5 | 5 | 5 | 5 | 5 | 5 | 0 | 0 |
| 38 | 10 | 5 | 5 | 5 | 5 | 5 | 5 | 5 | 0 | 0 |
|  | 5 | 5 | 5 | 5 | 5 | 5 | 4 | 5 | 0 | 0 |
|  | 2.5 | 5 | 5 | 4 | 5 | 4 | 3 | 3 | 0 | 0 |
|  | 10 | 5 | 5 | 5 | 5 | 5 | 5 | 5 | 1 | 2 |
| 4 | 5 | 5 | 5 | 5 | 5 | 5 | 5 | 5 | 0 | 0 |
|  | 2.5 | 5 | 5 | 5 | 5 | 5 | 5 | 5 | 0 | 0 |
|  | 1.25 | 5 | 5 | 5 | 5 | 5 | 5 | 5 | 0 | 0 |
|  | 10 | 5 | 5 | 5 | 5 | 5 | 5 | 5 | 0 | 1 |
| 5 | 5 | 5 | 5 | 5 | 5 | 5 | 5 | 5 | 0 | 0 |
|  | 2.5 | 5 | 5 | 5 | 5 | 5 | 5 | 5 | 0 | 0 |
|  | 1.25 | 5 | 5 | 5 | 5 | 5 | 5 | 5 | 0 | 0 |
|  | 20 | 5 | 5 | 5 | 5 | 5 | 5 | 5 | 0 | 0 |
| 6 | 5 | 5 | 5 | 5 | 5 | 5 | 5 | 0 | 0 |  |
|  | 5 | 5 | 5 | 5 | 5 | 5 | 4 | 5 | 0 |  |

TABLE 12-continued

| Comp. No. | Dose of Comp. (g/a) | Herbicidal effect | | | | | | | Phytotoxicity to crop plants | |
|---|---|---|---|---|---|---|---|---|---|---|
| | | W.A. | C.P. | P.P. | L.A. | S.G. | C.C. | P.S. | Corn | Soybean |
| | 2.5 | 5 | 5 | 4 | 5 | 4 | 3 | 5 | 0 | 0 |
| | 20 | 5 | 5 | 5 | 5 | 5 | 4 | 5 | 0 | 0 |
| Ref. F | 10 | 5 | 5 | 4 | 4 | 4 | 2 | 5 | 0 | 0 |
| | 5 | 4 | 5 | 3 | 3 | 3 | 1 | 4 | 0 | 0 |
| | 2.5 | 4 | 3 | 1 | 2 | 1 | 0 | 3 | 0 | 0 |
| | 20 | 5 | 5 | 5 | 5 | 5 | 3 | 5 | 0 | 0 |
| Ref. G | 10 | 5 | 5 | 4 | 5 | 4 | 2 | 4 | 0 | 0 |
| | 5 | 4 | 5 | 3 | 3 | 4 | 2 | 4 | 0 | 0 |
| | 2.5 | 3 | 2 | 1 | 2 | 1 | 0 | 3 | 0 | 0 |
| Non-treatment | — | 0 | 0 | 0 | 0 | 0 | 0 | 0 | 0 | 0 |

We claim:

1. A herbicidal composition comprising N-substituted-3, 4, 5, 6,-tetrahydrophthalimides which are represented by the formula:

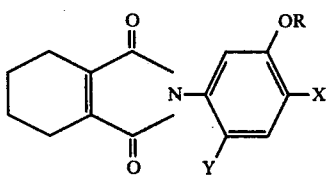

wherein X represents a chlorine or bromine atom: Y represents chlorine or hydrogen atom; wherein R represents a $C_3$-$C_4$ alkenyl group, a $C_3$-$C_4$ alkynyl group, or a $C_5$-$C_6$ cycloalkyl group, as an active ingredient, and a carrier, wherein said active ingredient is in a range of 0.5 to 80 weight % of the herbicidal composition.

2. A herbicidal composition according to claim 1 wherein the active ingredient is N-(3-propargyloxy-4-chlorophenyl)-3, 4, 5, 6-tetrahydrophthalimide.

3. A herbicidal composition according to claim 1 wherein the active ingredient is N-(3-propargyloxy bromophenyl)-3, 4, 5, 6-tetrahydrophthalimide.

4. A herbicidal composition according to claim 1 wherein the composition includes a surfactant.

5. A herbicidal composition according to claim 1 wherein R represents a propargyl group.

6. A herbicidal composition according to claim 1 wherein R represents an allyl or methallyl group.

7. A herbicidal composition according to claim 1 wherein R represents a cyclopentyl group or cyclohexyl group.

8. N-substituted-3, 4, 5, 6-tetrahydrophthalimides represented by the formula:

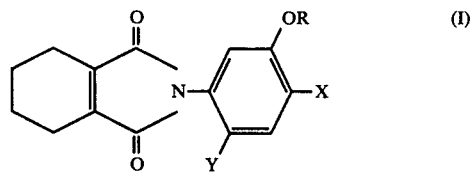

wherein X represents a chlorine or bromine atom; Y represents chlorine or hydrogen atom;
wherein R represents a $C_3$-$C_4$ alkenyl group, a $C_3$-$C_4$ alkynyl group or a $C_5$-$C_6$ cycloalkyl group.

9. N-substituted-3,4,5,6-tetrahydrophthalimides according to claim 8 wherein R represents a propargyl group.

10. N-substituted-3,4,5,6-tetrahydrophthalimides according to claim 8 wherein R represents allyl or methallyl group.

11. N-substituted-3,4,5,6-tetrahydrophthalimides according to claim 8 wherein R represents cyclopentyl group or cyclohexyl group.

12. N-substituted-3,4,5,6-tetrahydrophthalimides according to claim 10 wherein R represents an allyl group; Y represents a hydrogen atom and X represents chlorine or bromine atom.

13. N-(3-propargyloxy-4-chlorophenyl)-3,4,5,6-tetrahydrophthalimide.

14. N-(3-propargyloxy-4-bromophenyl)-3,4,5,6-tetrahydrophthalimide.

* * * * *